United States Patent [19]

Freedman et al.

[11] 4,096,210

[45] Jun. 20, 1978

[54] PROCESS FOR PREPARING PHOSPHOROTHIOATES AND PHENYLPHOSPHONOTHIOATES

[75] Inventors: Harold H. Freedman, Newton Center, Mass.; Stanley D. McGregor; Masao Yoshimine, both of Midland, Mich.; Lorraine M. Kroposki, Walnut Creek, Calif.

[73] Assignee: The Dow Chemical Company, Midland, Mich.

[21] Appl. No.: 742,144

[22] Filed: Nov. 15, 1976

Related U.S. Application Data

[62] Division of Ser. No. 585,554, Jun. 10, 1975, Pat. No. 4,007,197.

[51] Int. Cl.$^2$ .......................... C07F 9/165; C07F 9/40
[52] U.S. Cl. ............................ 260/973; 260/294.8 K; 544/243; 544/337
[58] Field of Search ............. 260/973, 250 B, 250 BP, 260/251 P

[56] References Cited

U.S. PATENT DOCUMENTS

| 3,972,887 | 8/1976 | Freedman | 260/250 B |
| 4,007,197 | 2/1977 | Freedman et al. | 260/294.8 K |

*Primary Examiner*—Jose Tovar
*Attorney, Agent, or Firm*—L. Wayne White

[57] ABSTRACT

Quaternary ammonium salts and sterically unhindered, nucleophilic, tertiary amines are novel cocatalysts which are used in the process of reacting an alkali metal phenate, pyridinate or pyrimidinate with an O,O-dialkylphosphorochloridothioate or O-alkyl phenylphosphonochloridothioate to produce the corresponding phosphorothioates and phenylphosphonothioates. The process is conducted under alkaline conditions in a liquid reaction medium.

12 Claims, No Drawings

PROCESS FOR PREPARING PHOSPHOROTHIOATES AND PHENYLPHOSPHONOTHIOATES

CROSS-REFERENCE TO RELATED APPLICATION

This is a division of application Ser. No. 585,554 filed June 10, 1975, now U.S. Pat. No. 4,007,197.

BACKGROUND OF THE INVENTION

The O-pyridyl phosphates and phosphorothioates were described by Rigterink in U.S. Pat. No. 3,244,586. Such compounds are particularly useful as insecticides and biocides. They are represented by Formula (I)

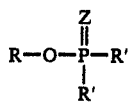
(I)

wherein R represents halopyridyl, Z represents oxygen or sulfur and each R' independently represents lower alkyloxy, amino or lower alkylamino. Rigterink disclosed several methods for preparing the compounds but his preferred method comprised reacting a phosphorochloridate or phosphorochloridothioate of Formula (II)

(II)

with an alkali metal or tertiary amine salt of a halopyridinol having the formula R—O-alkali metal or R—OH tertiary amine. The disclosed methods were carried out in an inert organic liquid under anhydrous conditions. In each of the disclosed processes an alkali metal chloride or the tertiary amine hydrochloride salt is produced as a reaction by-product which is removed by filtration. The disclosure of U.S. Pat. No. 3,244,586 is incorporated herein by reference.

Other phosphorothioates and phenylphosphonothioates have been similarly prepared and used. See, for example, the articles by O. Johnson in *Chemical Week*, pages 18–46 (26 July 1972) and by E. E. Kenaga and W. E. Allison in the *Bulletin of the Entomological Society of America*, Vol. 15, No. 2, pages 85–148 (June, 1969) which list many commercially available phosphorothioates and phenylphosphonothioates and which include U.S. patents pertaining to such compounds.

The phosphorothioates and phenylphosphonothioates referred to above and herein prepared correspond to the formulas

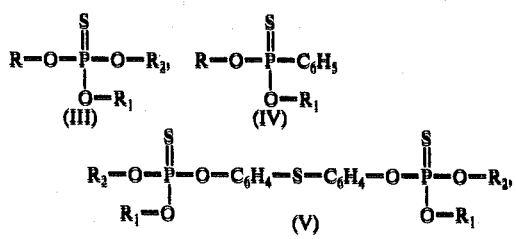

wherein: $R_1$ and $R_2$ are each independently lower alkyl; and R is

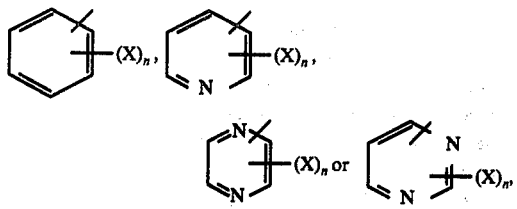

wherein:

n is 0, 1, 2 or 3; and

X is nitro, cyano, halo (fluoro, chloro, bromo and iodo, inclusive), lower alkyl, lower alkoxy, lower alkylthio or lower alkylsulfinyl, with the proviso that R does not bear more than one nitro group, lower alkylthio group or lower alkylsulfinyl group. By "lower alkyl" is meant in all instances alkyl of 1 to 4 carbon atoms (i.e. methyl, ethyl, propyl and butyl).

Compounds III–V are typically prepared by reacting (a) a compound corresponding to the formula

(VI)

or

(VII)

with (b) a compound corresponding to the formula

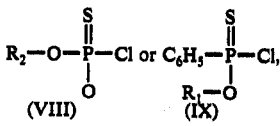

(VIII) (IX)

wherein M is an alkali metal (e.g. Na, K, etc.) and R, $R_1$ and $R_2$ have the aforesaid meaning. This reaction is normally conducted in an inert organic liquid reaction medium under alkaline conditions.

SUMMARY OF THE INVENTION

We have discovered novel compositions which catalyze the reaction between (a) and (b) above. When our new catalyst compositions are used, the phosphorothioates and phenylphosphonothioates (III–V) are obtained at commercially satisfactory reaction rates in excellent yields and purity. The use of our catalyst compositions therefore represents a process improvement in the known reaction between (a) and (b).

Our novel catalyst compositions are mixtures of:

(1) quaternary ammonium or phosphonium salts, and (2) organic, sterically unhindered, nucleophilic, tertiary amines exclusive of 1,4-diazabicyclo[2.2.2]octane and N-substituted diazoles.

The key to our invention resides in the discovery that said quaternary ammonium salts and said tertiary amines could be used as cocatalyst in the reaction between (a) and (b).

Amines alone have been used previously as catalyst and promote a high rate of reaction. However, the product (III–V) is normally thus obtained in lower yields than here obtained and contaminated with unacceptable amounts of by-products which must be removed. This necessitates an expensive and difficult purification step.

The quaternary ammonium salts can be used alone to catalyze the reaction and the product is obtained in quite pure form. However, at low catalyst concentration levels the reaction rate is generally too low to be commercially acceptable. At higher catalyst concentration levels, the reaction rate is higher, but it becomes increasingly difficult to remove the catalyst from the product.

We were therefore most surprised to discover that combinations of the quaternary ammonium salts and certain tertiary amines accelerated the reaction between (a) and (b) to a rate at least equivalent to that using the amine alone, and, in addition, increased the product yield at the expense of undesirable by-products.

DETAILED DESCRIPTION OF THE INVENTION

The Catalysts

The Quaternary Ammonium and Phosphonium Salts

Essentially any compound from the known class of quaternary ammonium and phosphonium salts can be used in the instant invention. Suitable quaternary ammonium and phosphonium salts have a minimum solubility of at least about 1 weight percent in the liquid reaction medium at 25° C and normally have a total aggregate carbon content of at least about 10 carbon atoms and preferably from about 12 to about 31 carbon atoms. The ammonium and phosphonium salts can be represented by the formula

wherein $R_1'$–$R_4'$ are hydrocarbyl groups (e.g., alkyl, aryl, alkaryl, aralkyl, cycloalkyl, etc.) and $Q^\oplus$ is a quaternized atom of nitrogen or phosphorus. Additionally, in (X) $R_1'$ can join with $R_2'$ to form a 5- or 6-membered heterocyclic compound having at least one quaternized nitrogen or phosphorus atom in the ring and may also contain one non-adjacent atom of nitrogen, oxygen or sulfur within the ring. Typically, $R_1'$–$R_4'$ in (X) are hydrocarbyl groups of from 1 to about 12 carbon atoms. $A^\ominus$ is an inert neutralizing anion and may be varied to convenience. By "inert" is meant inert in the instant process. Chloride and bromide are the preferred anions but other suitable anions include for example, fluoride, iodide, bisulfate, hydroxide, perchlorate, nitrate, acetate, tosylate, benzoate, and the like. The following compounds are illustrative: tetraalkyl ammonium salts, such as tetra-n-butyl-, tetrahexyl-, tri-n-butylmethyl-, cetyltrimethyl-, trioctylmethyl- and tridecylmethyl ammonium chlorides, bromides, bisulfates, tosylates, etc.; aralkylammonium salts, such as tetrabenzylammonium chloride, benzyltrimethyl-, benzyltriethyl-, benzyltributyl-, and phenethyltrimethyl- ammonium chlorides, bromides, etc.; arylammonium salts, such as triphenylmethylammonium fluoride, chloride or bromide, N,N,N-trimethylanilinium bromide, N,N-diethyl-N-methylanilinium bisulfate, trimethylnaphthylammonium chloride, p-methylphenyltrimethylammonium chloride or tosylate, etc.; 5- and 6-membered heterocyclic compounds containing at least one quaternized nitrogen atom in the ring, such as N-methylpyridinium chloride or methyl sulfate, N-hexyl pyridinium iodide, (4-pyridyl)-trimethylammonium chloride, 1-methyl-1-azabicyclo[2.2.1]heptane bromide, N,N-dibutylmorpholinium chloride, N-ethylthiazolium chloride, N-butylpyrrolium chlorides, etc., and the corresponding phosphonium salts and other like compounds.

The ammonium salts are currently preferred over the phosphonium salts due to cost and commercial availibility. The most preferred catalysts are benzyltrimethyl-, benzyltriethyl-, tetra-n-butyl and tri-n-butylmethyl ammonium salts.

The quaternary ammonium and phosphonium salts are used in the process in small but catalytic amounts. For example, amounts from about 0.1 to about 20 mole percent, based on the reactants, are suitable but amounts of from about 0.5 to about 10 mole percent are generally preferred.

The Tertiary Amines

The amines here used are organic, sterically unhindered, nucleophilic, tertiary amines exclusive of 1,4-diazabicyclo[2.2.2]octane and the N-substituted diazoles. Suitable amines for use herein will react with the phosphorochloridothioates and phenylphosphonochloridothioates (reactant (b) above) to form a 1:1 molar adduct of the amine and reactant (b) as a reactive intermediate. This adduct can be identified by any one of several conventional analytical techniques (e.g. by UV spectroscopy, etc.) at the command of one skilled in the art. As a viable alternative, however, the following screening technique can be used in most instances to ascertain whether a tertiary amine will or will not be an effective cocatalyst for use herein. The screening technique comprises blending equimolar quantities of the tertiary amine and reactant (b) in diethyl ether at room temperature and observing whether or not an ether-insoluble complex is formed. In essentially all instances, tertiary amines which are suitable catalysts for the stated reaction will form an ether-insoluble complex with reactant (b) within 15 minutes after mixing. Indeed, the more effective amine catalysts will produce the ether-insoluble complex essentially instantaneously upon mixing. Examples of suitable tertiary amines include aliphatic trihydrocarbyl amines (e.g. trimethylamine, ethyldimethylamine, butyldimethylamine, N,N,N',N'-tetramethylethylenediamine, and the like); aliphatic heterocyclic amines (e.g. 1-azabicyclo[2.2.2.]-octane, 1-methyl-2-imidazoline, 1-methylpyrrolidine, and the like); mixed aliphatic/aromatic amines (e.g. 4-(N,N-dimethyl amino)pyridine, 4-(N-pyrrolidino)-pyridine, phenyldimethylamine, and the like); and other like organic, sterically unhindered, nucleophilic, tertiary amines.

The tertiary amines are used in the instant process in small but catalytic amounts. For example, amounts of from about 0.25 to about 20 mole percent, based on the reactants, are suitable but amounts of from about 0.5 to about 10 mole percent are generally preferred.

Illustrative examples of suitable combinations of quaternary ammonium salts and tertiary amines include: benzyltriethyl phosphonium chloride and trimethylamine, benzyltriethylammonium bromide and trimethylamine, tetra-n-butylammonium bisulfate and 1-azabicyclo[2.2.2]octane, tri-n-butylmethylammonium bromide and 1-methylpyrrolidine, triphenylmethylphosphonium chloride and 4-(N,N-dimethylamino)-pyridine, tetra-n-butylphosphonium acetate and pyridine, 2,4-dichlorobenzyl trimethylammonium chloride and 3- or 4-picoline, tridecylmethylammonium chloride and 4-(N,N-dimethylamino)pyridine, octadecyl trimethyl ammonium bromide and trimethylamine, etc.

The Reactants

The alkali metal phenates, pyridinates and pyrimidinates are known classes of compounds corresponding to the formulas $$R-O^{\ominus}M^{\oplus} \text{ and } M^{\oplus\ominus}O-C_6H_4-S-C_6H_4-O^{\ominus}M^{\oplus},$$
$$\text{(VI)} \qquad\qquad \text{(VII)}$$

wherein R has the above meaning and M is an alkali metal (Li, Na, K, etc.) but is preferably sodium or potassium and is most preferably sodium.

The O,O-dialkyl phosphorochloridothioates and O-alkyl phenylphosphonochloridothioates are likewise well known classes of compounds which correspond to the formulas $$\underset{\underset{(VIII)}{R_1-O}}{\overset{\overset{S}{\parallel}}{R_2-O-P-Cl}} \text{ and } \underset{\underset{(IX)}{R_1-O}}{\overset{\overset{S}{\parallel}}{C_6H_5-P-Cl}}$$

wherein $R_1$ and $R_2$ are each independently lower alkyl but are preferably methyl or ethyl.

Various phosphorothioates and phenylphosphonothioates can obviously be prepared by using various combinations of the above reactants. Representative and illustrative lists of suitable reactants and combinations thereof are shown in Tables 1 and 2 below:

Table 1

$$\underset{\underset{}{R_1-O}}{\overset{\overset{S}{\parallel}}{R_2-O-P-Cl}} + R-O^{\ominus}M^{\oplus} \longrightarrow \underset{\underset{}{O-R_1}}{\overset{\overset{S}{\parallel}}{R-O-P-O-R_2}}$$

| No. | $R_1$ | $R_2$ | R | M |
|---|---|---|---|---|
| 1 | CH₃ | CH₃ | N=C(Cl)-CH=C(Cl)-CH=C(Cl)- (trichloropyridinyl) | Na |
| 2 | C₂H₅ | C₂H₅ | trichloropyridinyl | Na |
| 3 | C₂H₅ | C₂H₅ | fluoropyridinyl | Na |
| 4 | CH₃ | CH₃ | 2,4,5-trichlorophenyl | Na |
| 5 | C₂H₅ | C₂H₅ | 2,4-dichlorophenyl | K |

Table 1-continued $$\underset{\underset{}{R_1-O}}{\overset{\overset{S}{\parallel}}{R_2-O-P-Cl}} + R-O^{\ominus}M^{\oplus} \longrightarrow \underset{\underset{}{O-R_1}}{\overset{\overset{S}{\parallel}}{R-O-P-O-R_2}}$$

| No. | $R_1$ | $R_2$ | R | M |
|---|---|---|---|---|
| 6 | CH₃ | CH₃ | 2,5-dichloro-4-iodophenyl | Na |
| 7 | CH₃ | CH₃ | 2-chloro-4-nitrophenyl | Na |
| 8 | C₂H₅ | C₂H₅ | 4-nitrophenyl | Na |
| 9 | CH₃ | CH₃ | 4-nitrophenyl | K |
| 10 | CH₃ | CH₃ | 3-methyl-4-nitrophenyl | K |
| 11 | CH₃ | CH₃ | 3-methyl-4-(methylthio)phenyl | Na |
| 12 | C₂H₅ | C₂H₅ | 3-methyl-4-(methylsulfinyl)phenyl | Na |
| 13 | C₂H₅ | C₂H₅ | 4-(methylsulfinyl)phenyl | Na |
| 14 | C₂H₅ | C₂H₅ | 2-isopropyl-pyrimidin-4-yl | K |
| 15 | C₂H₅ | C₂H₅ | pyrazinyl | Na |
| 16 | CH₃ | CH₃ | 4-cyanophenyl | K |

Table 2

$$C_6H_5-\underset{R_1-O}{\overset{S}{\overset{\|}{P}}}-Cl + R-O^{\ominus}M^{\oplus} \longrightarrow R-O-\underset{O-R_1}{\overset{S}{\overset{\|}{P}}}-C_6H_5$$

| No. | R₁ | R | M |
|---|---|---|---|
| 17 | CH₃ | 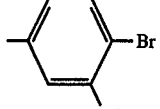 (4-Br, 2,6-diCl phenyl) | Na |
| 18 | C₂H₅ | 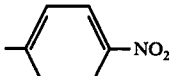 (4-NO₂ phenyl) | K |
| 19 | C₂H₅ | 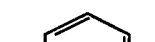 (4-CN phenyl) | Na |
| 20 | CH₃ | 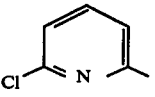 (3-Cl-2-pyridyl) | Na |
| 21 | C₂H₅ | 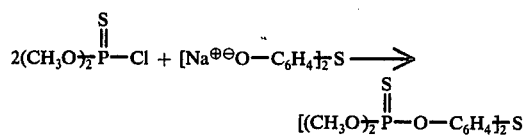 (3-Cl-2-pyridyl) | Na |

The compounds of Formula (V) are prepared in like manner. E.g.

$$2(CH_3O)_2\overset{S}{\overset{\|}{P}}-Cl + [Na^{\oplus\ominus}O-C_6H_4]_2S \longrightarrow$$

$$[(CH_3O)_2\overset{S}{\overset{\|}{P}}-O-C_6H_4]_2S$$

Process Parameters

The reaction proceeds at a satisfactory rate at temperatures of from about 0° C up to about 100° C with a preferred rate being obtained at temperatures of from about 40° to about 60° C. The reaction pressure is not critical and generally atmospheric or superatmospheric pressures are used as a matter of convenience. Under the above conditions, reaction times of up to 8 hours are common although reaction times of from 0.25 to 5 hours are generally sufficient for the reaction to be substantially complete.

Suitable such inert organic liquids include, for example, hydrocarbon solvents (e.g. benzene, toluene, xylene, cyclohexane, etc.), chlorinated hydrocarbon solvents (e.g. methylene chloride, chloroform, carbon tetrachloride, tetrachloroethylene, etc.), and the like. Also suitable are 2-phase mixtures of inert water-immiscible organic liquids and water (e.g. any of the aforesaid hydrocarbon or chlorinated hydrocarbon solvents and water). Methylene chloride or methylene chloride and water are the preferred reaction medium diluents.

The process is conducted under alkaline conditions. Such conditions can be easily achieved by conducting the process in the presence of caustic (NaOH) or other base or by use of an appropriate buffer system.

Agitation (e.g., stirring swirling, etc.) of the reaction mixture is advantageous, particularly when the process is conducted in the 2-phase liquid reaction medium (e.g. methylene chloride and water).

The following examples further illustrate the invention.

EXAMPLES 1-4

The reaction between O,O-diethylphosphorochloridothioate (9.5 g., 0.05 mole) and sodium 3,5,6-trichloro-2-pyridinate (12.0 g., 0.05 mole) in a mixture of methylene chloride and water was catalyzed by a mixture of benzyltrimethylammonium chloride [3 mole %] and 1-2 mole % each of the following amines:

1-azabicyclo[2.2.2]octane
trimethylamine
N-methylpyrrolidine
4-(N,N-dimethylamino)pyridine The product, O,O-diethyl O-3,5,6-trichloro-2-pyridylphosphorothioate, was thus produced in extremely high yields (i.e. greater than 90 percent of theory, based on reactants charged) and purity at reaction times of about 1 to 2 hours or less under reflux conditions. The product was recovered by separating the aqueous inorganic phase of the reaction mixture, washing the organic phase three times with water and subjecting the organic phase to fractional distillation to effect removal of the solvent from the product.

EXAMPLES 5-14

The product of Examples 1-4 was produced in excellent yields in substantially like manner using the catalyst combinations set forth in Table 3.

Table 3

| Ex. | N⊕ salt (mole %) | Amine (mole %) | Reaction Time (hrs) | Yield (%) |
|---|---|---|---|---|
| 5 | BTEAC (1) | 4-picoline (2) | 3.0 | 88.6 |
| 6 | BTEAC (2) | quinuclidine (2) | 1.1 | 94.2 |
| 7 | BTEAC (10) | C₆H₅-N(CH₃)₂(10) | 9.5 | 90.2 |
| 8 | BTEAC (10) | N-methyl-morpholine (10) | 9.0 | 90.8 |
| 9 | BTEAC (10) | tetramethyl-ethylenediamine (10) | 3.3 | 91.0 |
| 10 | BTEAC (10) | C₆H₅CH₂N(C₂H₅) (10) | 7.0 | 69.2 |
| 11 | BTEAC (10) | 4-(N,N-dimethylamino)pyridine (10) | 1.0 | 89.2 |
| 12 | BTEAC (10) | N(CH₃)₃(10) | 1.0 | 94.6 |
| 13 | BTEAC (1) | N(CH₃)₃ | 5.5 | 90.2 |
| 14 | (butyl)₄N⊕ Br⊖ (10) | 4-(N,N-dimethylamino) pyridine (10) | 0.7 | 99.7 |

In Table 3, "BTEAC" is an abbreviation for benzyltriethylammonium chloride.

Each of the amines in Table 3 formed an insoluble complex in diethyl ether within 15 minutes when mixed with an equimolar (0.01 mole) amount of O,O-diethyl phosphorochloridothioate in 10 ml of diethyl ether at room temperature.

Other quaternary ammonium and phosphonium salts and tertiary amines having the qualifications set forth above can be similarly used with good results in catalyzing the reaction to produce O,O-diethyl O-3,5,6-trichloro-2-pyridylphosphorothioate and other like phosphorothioates and phenylphosphonothioates.

We claim:

1. In the process of preparing a compound corresponding to the formula

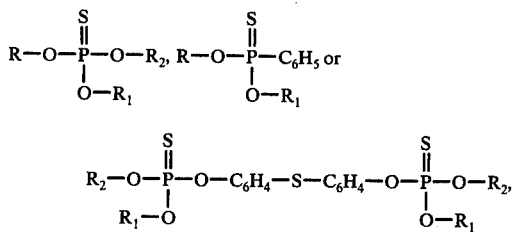

wherein:

$R_1$ and $R_2$ are each independently lower alkyl; and R is

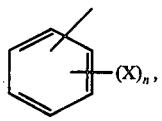

wherein:

$n$ is 0, 1, 2 or 3; and
X is nitro, cyano, halo, lower alkyl, lower alkoxy, lower alkylthio or lower alkylsulfinyl, with the proviso that R does not bear more than one nitro group, lower alkylthio group or lower alkylsulfinyl group; by reacting in an inert liquid reaction medium under alkaline conditions (a) a compound corresponding to the formula $R-O^{\ominus}M^{\oplus}$ or $M^{\oplus}O^{\ominus}-C_6H_4-S-C_6H_4-O^{\ominus}M^{\oplus}$ with (b) a compound corresponding to the formula

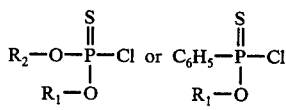

wherein M is an alkali metal and R, $R_1$ and $R_2$ have the aforesaid meaning;

the improvement consisting of conducting the process in the presence of a small but catalytic amount of (1) a quaternary ammonium or phosphonium salt having a minimum solubility of at least 1 weight percent in the liquid reaction medium at 25° C and (2) an organic, sterically unhindered, nucleophilic tertiary amine, with the proviso that said amine is not 1,4-diazabicyclo[2.2.2]octane or an N-substituted diazole when (1) is a quaternary ammonium salt.

2. The process defined in claim 1 wherein (1) is an ammonium or phosphonium salt of the formula $R_1'R_2'R_3'R_4'Q^{\oplus}A^{\ominus}$ wherein $Q^{\oplus}$ is a quaternized atom of nitrogen or phosphorus; and $R_1'-R_4'$ are each independently hydrocarbyl groups of from 1 to about 12 carbon atoms, or $R_1'$ is joined with $R_2'$ to form a 5- or 6-membered heterocyclic having at least one quaternized nitrogen atom within the ring and may additionally contain one non-adjacent atom of nitrogen, oxygen or sulfur within the ring; and $A^{\ominus}$ is a compatible neutralizing anion.

3. The process defined by claim 2 wherein (1) is a quaternary ammonium salt.

4. The process defined in claim 2 wherein (1) is a benzyltrimethyl-, benzyltriethyl-, tetra-n-butyl- or tri-n-butylmethylammonium salt.

5. The process defined in claim 3 wherein (1) is benzyltrimethylammonium chloride, benzyltriethylammonium chloride or tetra-n-butylammonium bisulfate.

6. The process defined in claim 1 wherein $R_1$ and $R_2$ are methyl or ethyl.

7. The process defined in claim 6 wherein R is

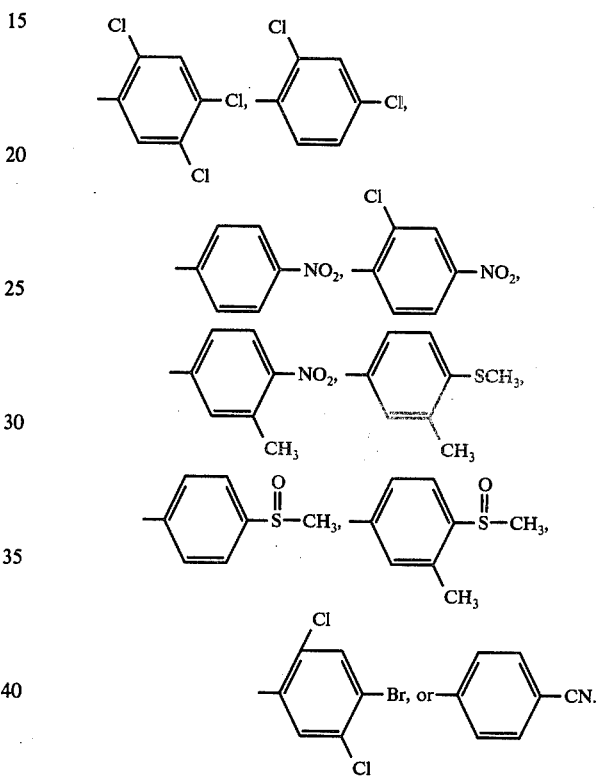

8. The process defined by claim 7 wherein (1) is benzyltrimethylammonium chloride or benzyltriethylammonium chloride.

9. The process defined in claim 8 wherein (2) is 1-azabicyclo[2.2.2]octane, trimethylamine, N-methylpyrrolidine, 4-(N,N-dimethylamino)pyridine, 4-picoline, phenyldimethylamine, N-methylmorpholine, tetramethylethylenediamine, or benzyldiethylamine.

10. The process defined in claim 1 wherein (2) is 4-(N,N-dimethylamino)pyridine.

11. The process defined in claim 1 wherein said process is conducted in an agitated 2-phase solvent system consisting of an inert water-immiscible organic liquid and water.

12. The process defined in claim 8 wherein said process is conducted in an agitated 2-phase solvent system consisting of an inert water-immiscible organic liquid and water.

* * * * *

UNITED STATES PATENT AND TRADEMARK OFFICE
CERTIFICATE OF CORRECTION

PATENT NO. : 4,096,210
DATED : June 20, 1978
INVENTOR(S) : Harold H. Freedman et al.

It is certified that error appears in the above-identified patent and that said Letters Patent are hereby corrected as shown below:

Column 2, between lines 31 and 37 Formula VIII should read as follows:

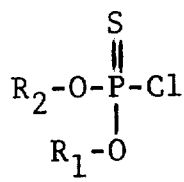

Column 7, line 67, insert -- , -- between "stirring swirling";

Column 8, line 46, Table 3, Compound 10 under column heading "Amine (mole%)" should read -- $C_6H_5CH_2N(C_2H_5)_2$ --.

Signed and Sealed this

Twenty-sixth Day of December 1978

[SEAL]

Attest:

RUTH C. MASON
Attesting Officer

DONALD W. BANNER
Commissioner of Patents and Trademarks